(12) United States Patent
Xu et al.

(10) Patent No.: US 8,995,747 B2
(45) Date of Patent: Mar. 31, 2015

(54) METHODS, SYSTEMS AND APPARATUS FOR DEFECT DETECTION AND CLASSIFICATION

(75) Inventors: Xinyu Xu, Vancouver, WA (US); Chang Yuan, Vancouver, WA (US); Masakazu Yanase, Vancouver, WA (US)

(73) Assignee: Sharp Laboratories of America, Inc., Camas, WA (US)

( * ) Notice: Subject to any disclaimer, the term of this patent is extended or adjusted under 35 U.S.C. 154(b) by 815 days.

(21) Appl. No.: 12/846,766

(22) Filed: Jul. 29, 2010

(65) Prior Publication Data

US 2012/0027286 A1 Feb. 2, 2012

(51) Int. Cl.
*G06K 9/00* (2006.01)
*G01N 21/95* (2006.01)
*G01N 21/88* (2006.01)
*G06T 7/00* (2006.01)

(52) U.S. Cl.
CPC ............ *G01N 21/95* (2013.01); *G01N 21/8851* (2013.01); *G06T 7/0008* (2013.01); *G06T 7/001* (2013.01); *G06T 2207/30121* (2013.01); *G01N 2021/8854* (2013.01); *G01N 2021/9513* (2013.01)
USPC ......................................................... 382/149

(58) Field of Classification Search
None
See application file for complete search history.

(56) References Cited

U.S. PATENT DOCUMENTS

| | | | |
|---|---|---|---|
| 5,081,687 A * | 1/1992 | Henley et al. | 382/141 |
| 5,459,410 A * | 10/1995 | Henley | 324/760.02 |
| 6,028,580 A * | 2/2000 | Kosegawa et al. | 345/98 |
| 6,154,561 A * | 11/2000 | Pratt et al. | 382/141 |
| 6,356,300 B1 | 3/2002 | Shiba | |
| 6,456,899 B1 | 9/2002 | Gleason et al. | |
| 6,882,896 B2 | 4/2005 | Ting et al. | |
| 6,922,482 B1 | 7/2005 | Ben-Porath | |
| 6,987,873 B1 | 1/2006 | Ben-Porath et al. | |
| 7,003,146 B2 | 2/2006 | Eck et al. | |
| 7,132,652 B1 | 11/2006 | Testoni | |
| 7,196,785 B2 | 3/2007 | Nishiyama et al. | |
| 7,330,581 B2 | 2/2008 | Ishikawa | |
| 7,425,704 B2 | 9/2008 | Miyai et al. | |
| 7,508,973 B2 | 3/2009 | Okabe et al. | |
| 7,538,750 B2 | 5/2009 | Kim et al. | |
| 7,583,832 B2 | 9/2009 | Okuda et al. | |
| 7,761,182 B2 | 7/2010 | Gallarda et al. | |
| 2001/0020194 A1 | 9/2001 | Takagi et al. | |

(Continued)

FOREIGN PATENT DOCUMENTS

| | | |
|---|---|---|
| JP | 2008158501 A | 7/2008 |
| JP | 2010066186 A | 3/2010 |
| WO | 2008/015738 A1 | 7/2008 |

OTHER PUBLICATIONS

Cordelia Schmid, Roger Mohr and Christian Bauckhage, "Evaluation of Interest Point Detectors," International Journal of Computer Vision, Jun. 2000, pp. 151-172, vol. 37, Issue 2, Kluwer Academic Publishers, The Netherlands.

(Continued)

*Primary Examiner* — Paul Danneman
(74) *Attorney, Agent, or Firm* — Kristine Elizabeth Matthews; David C. Ripma

(57) ABSTRACT

Aspects of the present invention are related to systems, methods and apparatus for image-based automatic detection of a defective area in a flat panel display and classification of the defect type and the cause of the detected defect.

14 Claims, 10 Drawing Sheets

(56) References Cited

U.S. PATENT DOCUMENTS

| | | | |
|---|---|---|---|
| 2006/0226865 A1 | 10/2006 | Gallarda et al. | |
| 2008/0004742 A1 | 1/2008 | Hirai et al. | |
| 2008/0313893 A1* | 12/2008 | Nakasu | 29/830 |
| 2009/0028423 A1* | 1/2009 | Sandstrom et al. | 382/149 |
| 2009/0136117 A1 | 5/2009 | Barkol et al. | |
| 2009/0224777 A1 | 9/2009 | Kim et al. | |

OTHER PUBLICATIONS

Pierre Moreels and Pietro Perona, "Evaluation of Features Detectors and Descriptors based on 3D Objects," International Journal of Computer Vision, 2006, pp. 263-284, vol. 73, Issue 3, Springer Science + Business Media, USA.

E De Castro and C Morandi, "Registration of Translated and Rotated Images Using Finite Fourier Transforms," IEEE Transactions on Pattern Analysis and Machine Intelligence, Sep. 1987, pp. 700-703, vol. 9, Issue 5, IEEE Computer Society, Washington, DC, USA.

Christopher J.C. Burges, "A Tutorial on Support Vector Machines for Pattern Recognition," Data Mining and Knowledge Discovery 2, 1998, pp. 121-167.

Yoav Freund and Robert E. Schapire, "Experiments with a New Boosting Algorithm," in Proceedings of the Thirteenth International Conference on Machine Learning (ICML '96), Jul. 1996, pp. 148-156, Bari, Italy.

Steve Marschner, "2D Geometric Transformations," located at http://www.cs.cornell.edu/Courses/cs465/2006fa/lectures/07transforms2d.ppt.pdf, Fall 2006, Cornell CS 465 Fall 2006, Lecture 7, Cornell.

Japanese Office Action—Patent Application 2011-052175—Mailing Date: Feb. 25, 2014.

* cited by examiner

METHODS, SYSTEMS AND APPARATUS FOR DEFECT DETECTION AND CLASSIFICATION

FIELD OF THE INVENTION

Embodiments of the present invention relate, in general, to defect detection and defect-type and defect-cause classification. More specifically, embodiments of the present invention relate to image-based automatic detection of a defective area in a flat panel display and classification of the defect type and the cause of the detected defect.

BACKGROUND

Flat panel displays (FPDs) are becoming increasing prevalent in a wide variety of consumer products, for example, cell phones, digital cameras, liquid crystal display (LCD) televisions, computer displays, personal digital assistances (PDAs) and other consumer products comprising a display. To ensure the display quality and to improve the yield of FPDs, the inspection of FPDs for defects and the classification of the defects and classification of the cause of a defect may be crucial tasks in FPD manufacturing.

One conventional approach to defect detection and type and cause classification is by manual, human inspection. In such approaches, a human operator may need to examine each image of a FPD to identify a defective area, or areas, and to manually label the defects and their causes. This human process may depend heavily on the skills and expertise of the operator. Additionally, the time required to process different images may be significantly different, which may cause a problem for a mass-production pipeline. Furthermore, the working performance may vary considerably between human operators and may drop quickly over time due to operator fatigue. Traditional manual inspection may be slow, subjective, costly and highly dependent on the experience of the inspector due to the fact that the FPD surface pattern may be very complex and may vary widely between different sensed images.

Fast, robust, automatic and accurate methods, systems and apparatus that can perform defect detection and defect-type and defect-cause classification on different images of FPDs may be desirable.

SUMMARY

Embodiments of the present invention relate, in general, to defect detection and defect-type and defect-cause classification. More specifically, embodiments of the present invention relate to image-based automatic detection of a defective area in a flat panel display and classification of the defect type and the cause of the detected defect. In some embodiments of the present invention, a repair method associated with the detected defect may be identified.

According to a first aspect of the present invention, a defect type associated with a detected defect may be identified. The defect type may be identified using a classification tree based on connectivity measures between the detected defect and landmarks in said flat panel display and based on distance measures between the detected defect and the landmarks.

According to a second aspect of the present invention, a defect cause associated with a detected defect may be identified. The defect cause may be identified using a combination of rule-based classification and learning-based classification.

According to a third aspect of the present invention, multiple defect blobs returned by defect detection may be merged into a single defect by assigning the multiple defect blobs the same index label.

The foregoing and other objectives, features, and advantages of the invention will be more readily understood upon consideration of the following detailed description of the invention taken in conjunction with the accompanying drawings.

BRIEF DESCRIPTION OF THE SEVERAL DRAWINGS

DETAILED DESCRIPTION OF EXEMPLARY EMBODIMENTS

Embodiments of the present invention will be best understood by reference to the drawings, wherein like parts are designated by like numerals throughout. The figures listed above are expressly incorporated as part of this detailed description.

It will be readily understood that the components of the present invention, as generally described and illustrated in the figures herein, could be arranged and designed in a wide variety of different configurations. Thus, the following more detailed description of the embodiments of the methods and systems of the present invention is not intended to limit the scope of the invention but it is merely representative of the presently preferred embodiments of the invention.

Elements of embodiments of the present invention may be embodied in hardware, firmware and/or software. While exemplary embodiments revealed herein may only describe one of these forms, it is to be understood that one skilled in the art would be able to effectuate these elements in any of these forms while resting within the scope of the present invention.

Embodiments of the present invention relate, in general, to defect detection and defect-type and defect-cause classification. More specifically, embodiments of the present invention relate to image-based automatic detection of a defective area in a flat panel display (FPD) and classification of the defect type and the cause of the detected defect.

Figure 1:
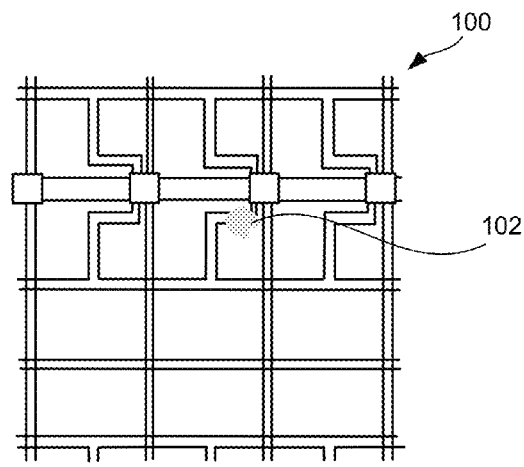
FIG. 1 is an illustration of an exemplary flat panel display with a defect.

According to some embodiments of the present invention, a digital image of an FPD may be acquired from one, or more, digital cameras in order to assess whether or not the FPD comprises a defective area, and, if so, to identify the defective area and classify the defect and the cause of the defect. FIG. 1 illustrates a portion 100 of an exemplary flat panel display structure comprising an LCD three color component pixel with a defect 102.

Some embodiments of the present invention may comprise methods, systems and apparatus for categorizing a defect on a flat panel display into one of a plurality of predefined defect types based on the location of the defect and prior knowledge of the topological structure of the flat panel display. Some embodiments of the present invention may comprise methods, systems and apparatus for inferring the cause of a detected defect.

Figure 2:
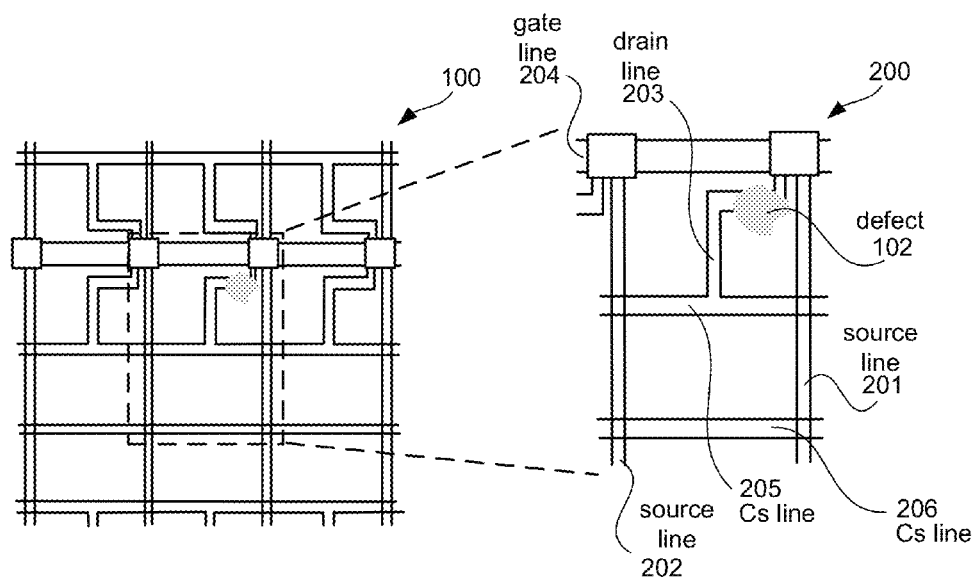
FIG. 2 is an illustration of exemplary landmarks in an image of an exemplary flat panel display.

In some embodiments of the present invention, defect-type classification and defect-cause classification may rely on the position of the defect with respect to landmarks within the flat panel display. Exemplary landmarks may include gate lines, drain lines, Cs lines, source lines and other components integral to a flat panel display. FIG. 2 depicts exemplary landmarks 201-206 for a sub-pixel portion 200 of the exemplary flat panel display structure 100 shown in FIG. 1.

In some embodiments of the present invention, landmark mask images may be extracted from a defect-free model image associated with a flat panel display pixel. In some embodiments of the present invention, the landmark mask images may be segmented from the defect-free model image using automatic segmentation methods known in the art. In alternative embodiments of the present invention, the landmark mask images may be segmented from the defect-free model image manually. In still alternative embodiments of the present invention, the landmark mask images may be semi-automatically segmented from the defect-free model image.

Figure 3:
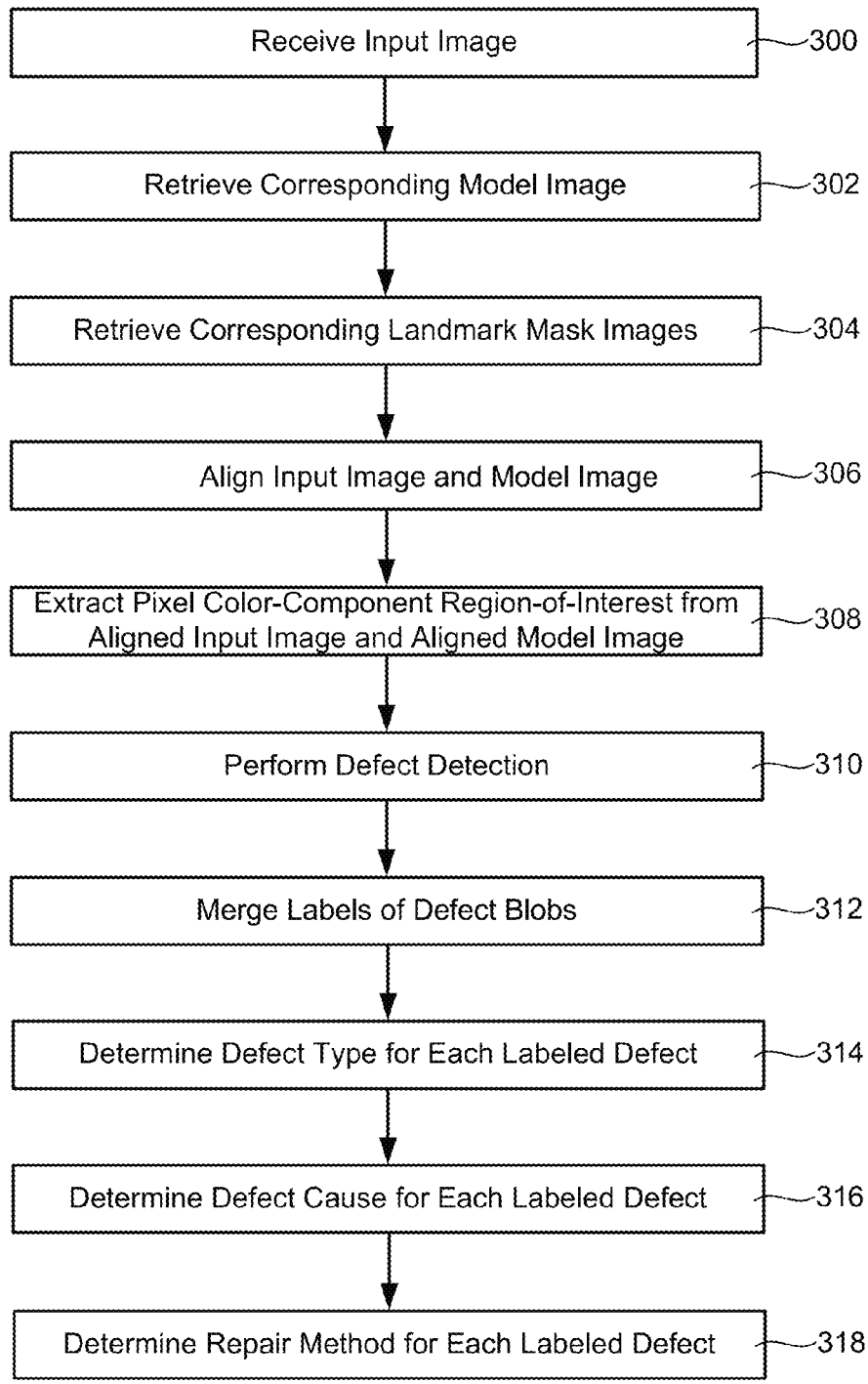
FIG. 3 is a chart showing exemplary embodiments of the present invention comprising defect detection, defect-type classification, defect-cause classification and determination of a defect repair method.

Some embodiments of the present invention may be understood in relation to FIG. 3. In these embodiments, an input image associated with a flat panel display maybe received 300, and a corresponding model image may be retrieved 302. Additionally, a plurality of landmark mask images associated with the model image may be retrieved. The input image and the model image may be aligned 306 using alignment methods, systems and apparatus known in the art, for example, the methods, systems and apparatus disclosed in U.S. patent application Ser. No. 12/846,748, "Methods, Systems and Apparatus for Defect Detection," invented by Chang Yuan, Masakazu Yanase and Xinyu Xu and filed on Jul. 29, 2010, which is hereby incorporated by reference herein in its entirety. In some embodiments of the present invention, the model image may be transformed to the coordinate system of the input image using an estimated transform determined in the alignment process. In alternative embodiments of the present invention, the input image may be transformed to the coordinate system of the model image using an estimated transform determined in the alignment process. In yet alternative embodiments, both the input image and the model image may be transformed to a common, third coordinate system using the estimated transform determined in the alignment process. A pixel color-component, also considered sub-pixel, region-of-interest (ROI) may be extracted 308 from the both the aligned input image and the aligned model image, and defect detection may be performed 310 using the input image ROI and the model image ROI. Defect detection may be performed 310 using detection methods, systems and apparatus known in the art, for example, the methods, systems and apparatus disclosed in U.S. patent application Ser. No. 12/846,748. An indexed defect mask image may be generated by the defect detection, wherein each index may be associated with a defect blob within the defect mask. The labels of the defect blobs may be merged 312, and a defect-type may be determined 314 for each resulting labeled defect. Additionally, a defect-cause may be determined 316 for each resulting labeled defect, and a repair-method may be determined 318 for each resulting labeled defect. In alternative embodiments of the present invention, one, or more, of the determination of defect type, determination of defect cause and determination of repair method may not be performed.

Figure 4:
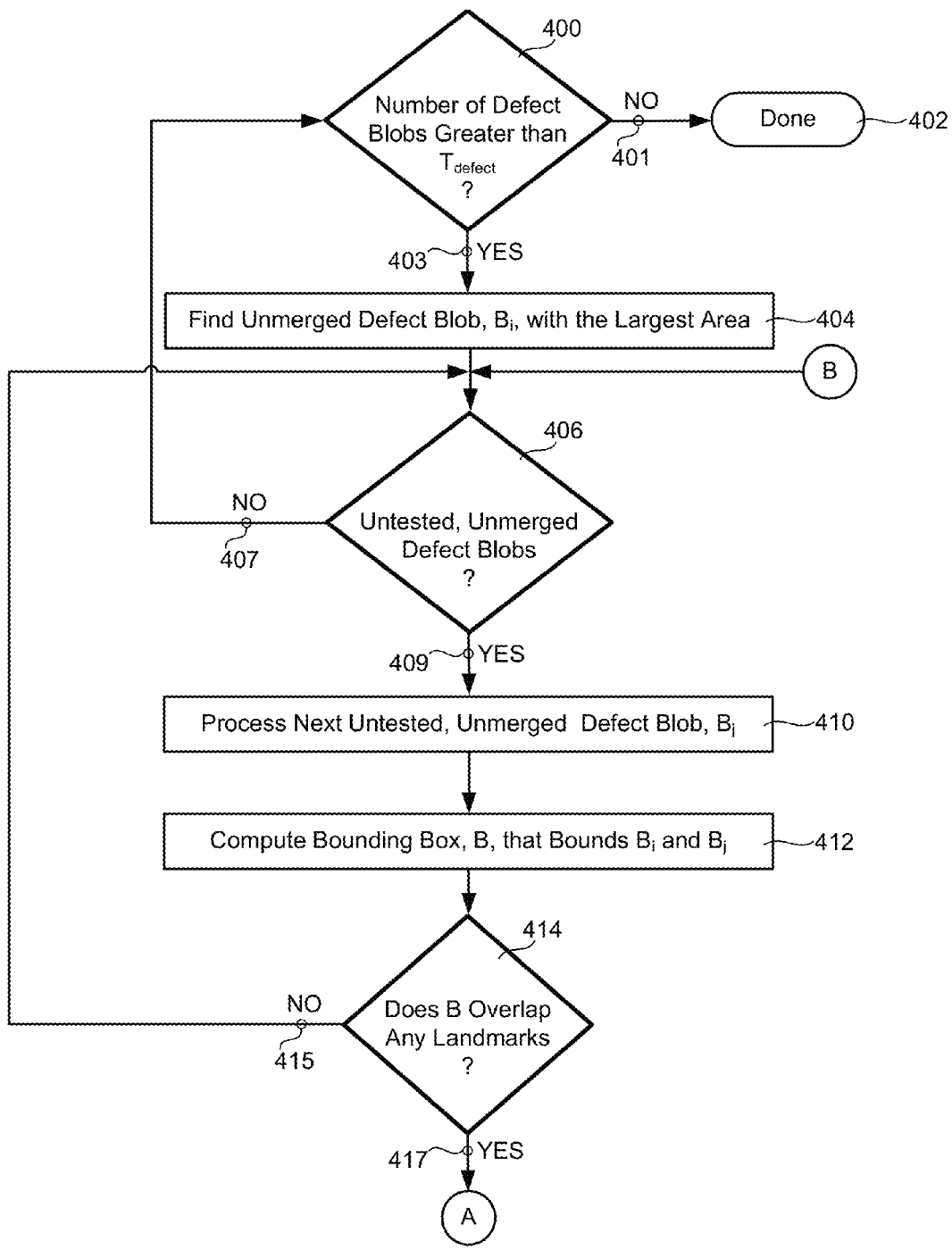
FIG. 4 is a chart showing exemplary embodiments of the present invention comprising merging of detected defect blob labels.
Figure 4:
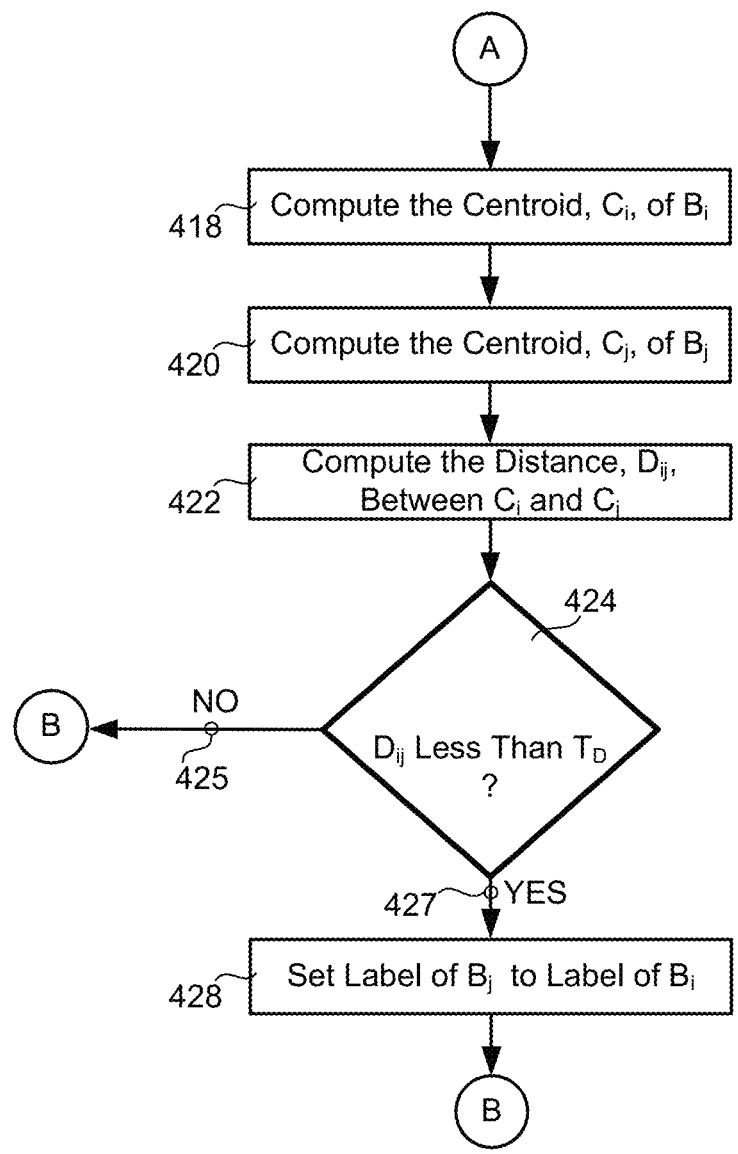

In some embodiments of the present invention understood in relation to FIG. 4, multiple defect blobs returned by the defect detection may be merged into a single defect by assigning the multiple defect blobs the same index label. Initially, the number of defect blobs may be compared 400 to a threshold value, which may be denoted $T_{defect}$, and if the number of defect blobs is less than or equal to 401 the threshold value, $T_{defect}$, then the merging process may terminate 402. If the number of defect blobs is greater than 403 the threshold value, $T_{defect}$, then the unmerged defect blob with the largest area may be determined 404. This defect blob may be denoted $B_i$. A determination 406 may then be made as to whether or not there are untested, unmerged defect blobs remaining. If there are not 407, then the merging process may continue by determining if the current number of defect blobs is still greater than the threshold value, $T_{defect}$. If there are 409 untested, unmerged defect blobs, then the next untested, unmerged, defect blob, which may be denoted $B_j$, may be processed 410. A bounding box, which may be denoted B, that bounds $B_i$ and $B_j$ may be computed 412. A determination 414 may be made as to whether or not the bounding box, B, overlaps any landmark mask images. If not 415, then the next untested, unmerged defect blob, if remaining, may be tested. If so 417, then the centroid of which may be denoted $C_i$, may be computed 418, and the centroid of $B_j$, which may be denoted $C_j$, may be computed 420. The distance, which may be denoted $D_{ij}$, between $C_i$ and $C_j$ may be computed 422 using any distance metric known in the art. The distance, $D_{ij}$, may be compared 424 to a distance threshold, which may be denoted $T_D$, and if $D_{ij}$ is not less than 425 $T_D$, then the next untested, unmerged defect blob, if remaining, may be tested. If $D_{ij}$ is less than 427, then the label of defect blob $B_j$ may be set 428 to the label of defect blob $B_i$, and then the next untested, unmerged defect blob, if remaining, may be tested. Thus, multiple defect blobs may be associated with a single index label and treated as one defect for defect-type determination, defect-cause determination and repair-method determination.

Figure 5:
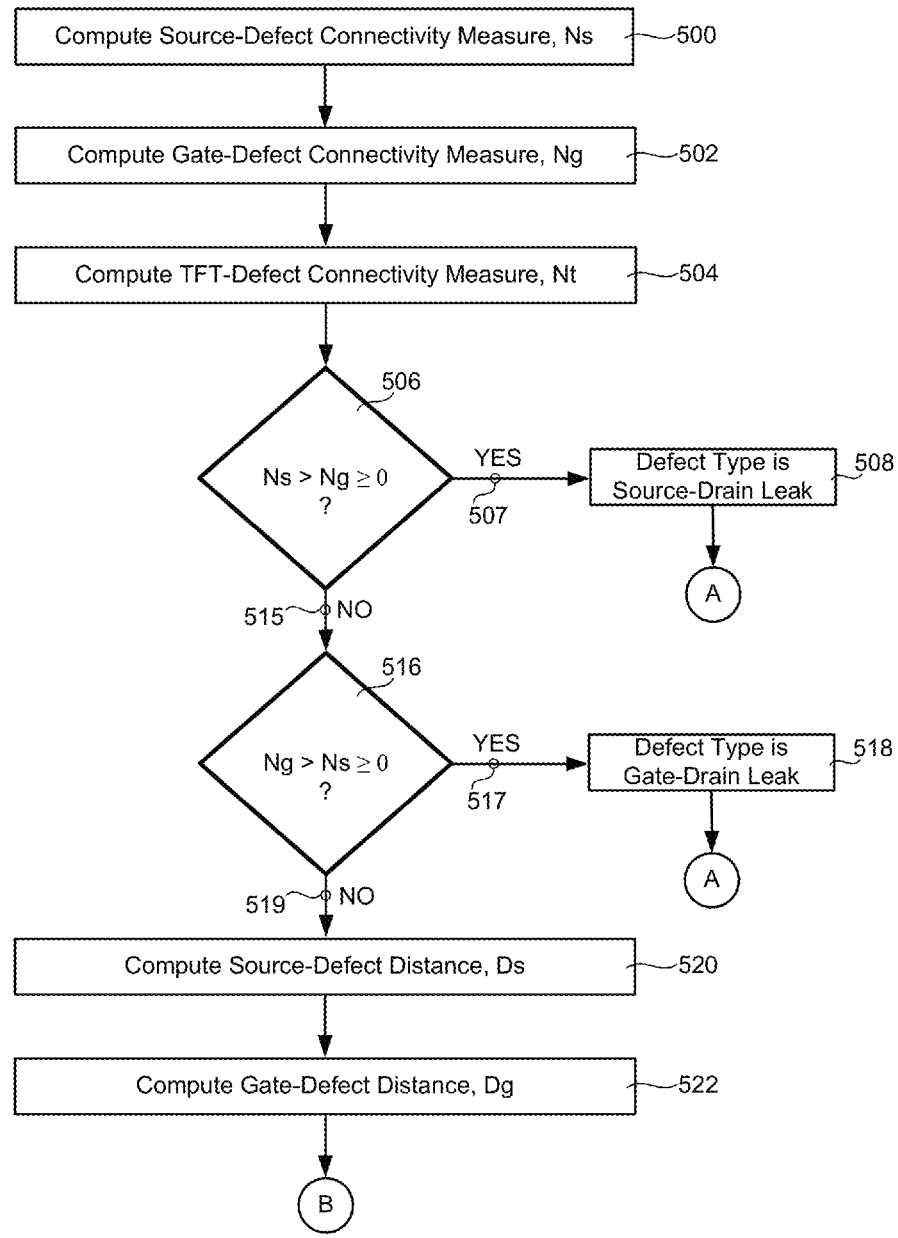
FIG. 5 is a chart showing exemplary embodiments of the present invention comprising a classification tree for defect-cause classification.
Figure 5:
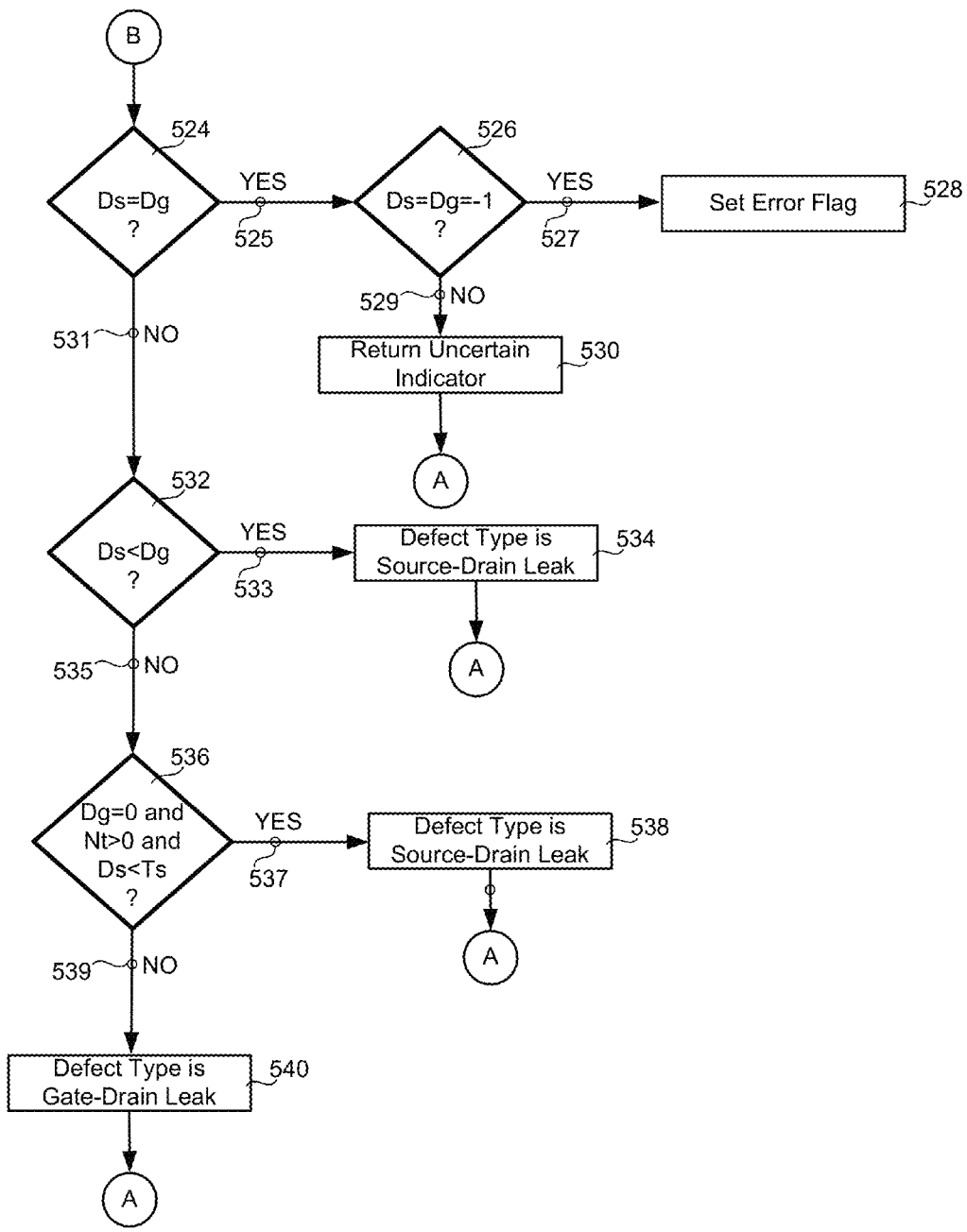
Figure 5:
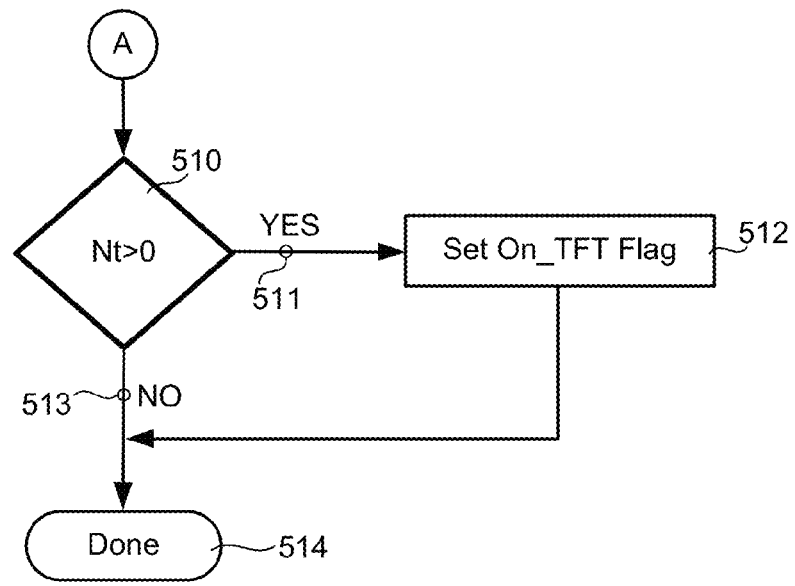

In some embodiments of the present invention, defect-type determination for a defect may comprise a decision tree and may be understood in relation to FIG. 5. In these exemplary embodiments, a source-defect connectivity measure indicating the connectivity between a defect and a source line may be computed 500 and may be denoted Ns. In some embodiments, the source-defect connectivity measure may be computed by determining the number of pixels in the defect overlapping the source line. A gate-defect connectivity measure indicating the connectivity between the defect and a gate line may be computed 502 and may be denoted Ng. In some embodiments, the gate-defect connectivity measure may be computed by determining the number of pixels in the defect overlapping the gate line. A TFT-defect connectivity measure indicating the connectivity between the defect and a TFT may be computed 504 and may be denoted Nt. In some embodiments, the TFT-defect connectivity measure may be computed by determining the number of pixels in the defect overlapping the TFT. In alternative embodiments of the present invention, other measures of connectivity, other than overlap count, may be used.

A comparison 506 may be made between Ns and Ng to determine if Ns is greater than Ng. If Ns is greater than Ng 507, then the defect type associated 508 with the defect may be a source-drain leak. A comparison 510 may be made between Nt and zero, and if Nt is greater than zero 511, then a flag indicating that the defect is located on the TFT may be set 512, and the detect-type classification may terminate 514. If Ns is not greater than Ng 515, then a comparison 516 may be made between Ns and Ng to determine if Ng is greater than Ns. If Ng is greater than Ns 517, then the defect type associated 518 with the defect may be a gate-drain leak. A comparison 510 may be made between Nt and zero, and if Nt is greater than zero 511, then a flag indicating that the defect is located on the TFT may be set 512, and the detect-type classification may terminate 514. If Ng is not greater than Ns 519, then a source-defect distance, which may be denoted Ds, from the defect to the source line may be computed 520, and a gate-defect distance, which may be denoted Dg, from the defect to the gate line may be computed 522. A comparison 524 may be made between Ds and Dg. If they are equal 525, then a determination 526 may be made as to whether or not they are equal to negative one. If they are equal to negative one 527, then an error flag may be set 528. If they are not equal to negative one 529, then an indicator that the classification process cannot classify the defect with certainty may be set 530. Then a comparison 510 may be made between Nt and zero, and if Nt is greater than zero 511, then a flag indicating that the defect is located on the TFT may be set 512, and the detect-type classification may terminate 514. If Ds is not equal to Dg 531, then a determination 532 may be made as to whether or not Ds is less than Dg. If Ds is less than Dg 533, then the defect type associated 534 with the defect may be a source-drain leak. A comparison 510 may be made between Nt and zero, and if Nt is greater than zero 511, then a flag indicating that the defect is located on the TFT may be set 512, and the detect-type classification may terminate 514. If Ds is not less than Dg 535, then a comparison 536 may be made to determine if Dg is equal to zero and Nt is greater than zero and Ds is less than a threshold, denoted Ts. If all of these conditions are met 537, then the defect type associated 538 with the defect may be a source-drain leak. A comparison 510 may be made between Nt and zero, and if Nt is greater than zero 511, then a flag indicating that the defect is located on the TFT may be set 512, and the detect-type classification may terminate 514. If any of these conditions are not met 539, then the defect type associated 540 with the defect may be a gate-drain leak. A comparison 510 may be made between Nt and zero, and if Nt is greater than zero 511, then a flag indicating that the defect is located on the TFT may be set 512, and the detect-type classification may terminate 514.

In some embodiments of the present invention, computing the number of defect pixels overlapping with a landmark may comprise a logical AND operation between the defect mask image and the landmark mask image. If the defect location in the defect mask image is indicated by non-zero pixel values and the landmark location in the landmark mask image is indicated by non-zero pixel values, then the overlap between the two may be the number of non-zero pixels resulting from the logical AND operation. A person of ordinary skill in the art will recognize that there are a number of ways to determine the number of defect pixels overlapping with a landmark.

In some embodiments of the present invention, the distance from a defect to a line of interest, for example, a source line or a gate line, may be computed by a distance transform using a distance metric, for example, the Manhattan distance metric, the Euclidean distance metric, the L1 distance metric, and other distance metrics known in the art. The distance transform may be used to determine the distance between the line of interest and the defect. The distance transform may be used to determine the distance to the nearest defect pixel at each pixel location in the input image.

Figure 6:
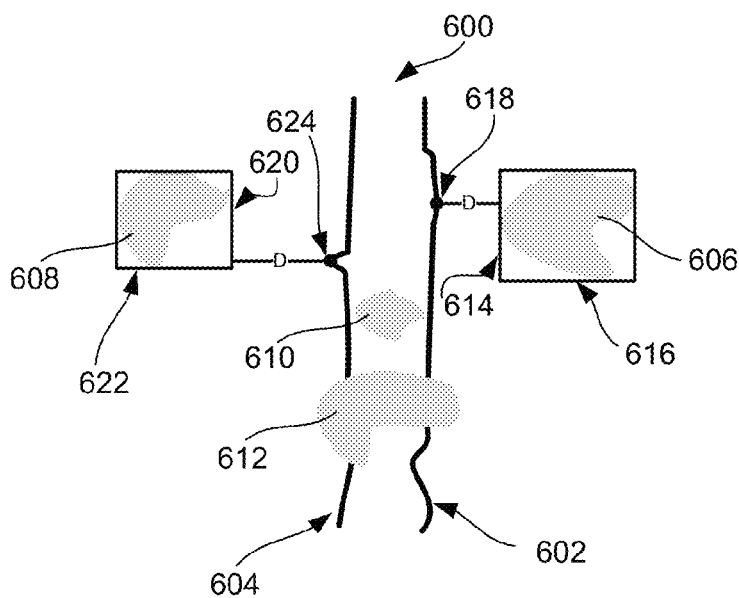
FIG. 6 is a picture illustrating calculation of the distance from a defect to a source line, according to embodiments of the present invention, for exemplary defect locations.

In alternative embodiments of the present invention, the distance from a defect to a source line may be computed according to:

$$Ds=\min (D_{ls}, D_{rs}),$$

where $D_{ls}$ and $D_{rs}$ may denote the distance to the left source line and the right source line, respectively. Computation of the distance to the left source line and the distance to the right source line may be described in relation to FIG. 6. FIG. 6 depicts and exemplary source line 600, for example, a right source line or a left source line, with a right edge 602 and a left edge 604. FIG. 6 also depicts four defects: a first defect 606 to the right of the source line 600, a second defect 608 to the left of the source line 600, a third defect 610 within the source line 600 and a fourth defect 612 extending beyond, or covering, the source line 600. For defects within 610 or extending beyond 612 the source line the distance to the source line may be zero. Thus, for a left source line, $D_{ls}=0$, and for a right source line, $D_{rs}=0$. For a defect 606 to the right of a source line 600, the distance to the source line 600 may be determined according to:

$$D=X_{defect\_bbox\_left}-X_{right\_most},$$

where D may denote either the distance, $D_{rs}$, to the right source or the distance, $D_{ls}$, to the left source line, depending on which is being computed, $X_{defect\_bbox\_left}$ may denote the x-coordinate of the left edge 614 of the bounding box 616 of the defect 606 and $X_{right\_most}$ may denote x-coordinate of the right-most pixel 618 on the right edge 602 of the source line 600. For a defect 608 to the left of a source line 600, the distance to the source line 600 may be determined according to:

$$D=X_{left\_most}-X_{defect\_bbox\_right},$$

where D may denote either the distance, $D_{rs}$, to the right source or the distance, $D_{ls}$, to the left source line, depending on which is being computed, $X_{defect\_bbox\_right}$ may denote the x-coordinate of the right edge 620 of the bounding box 622 of the defect 608 and $X_{left\_most}$ may denote x-coordinate of the left-most pixel 624 on the left edge 604 of the source line 600.

Figure 7:
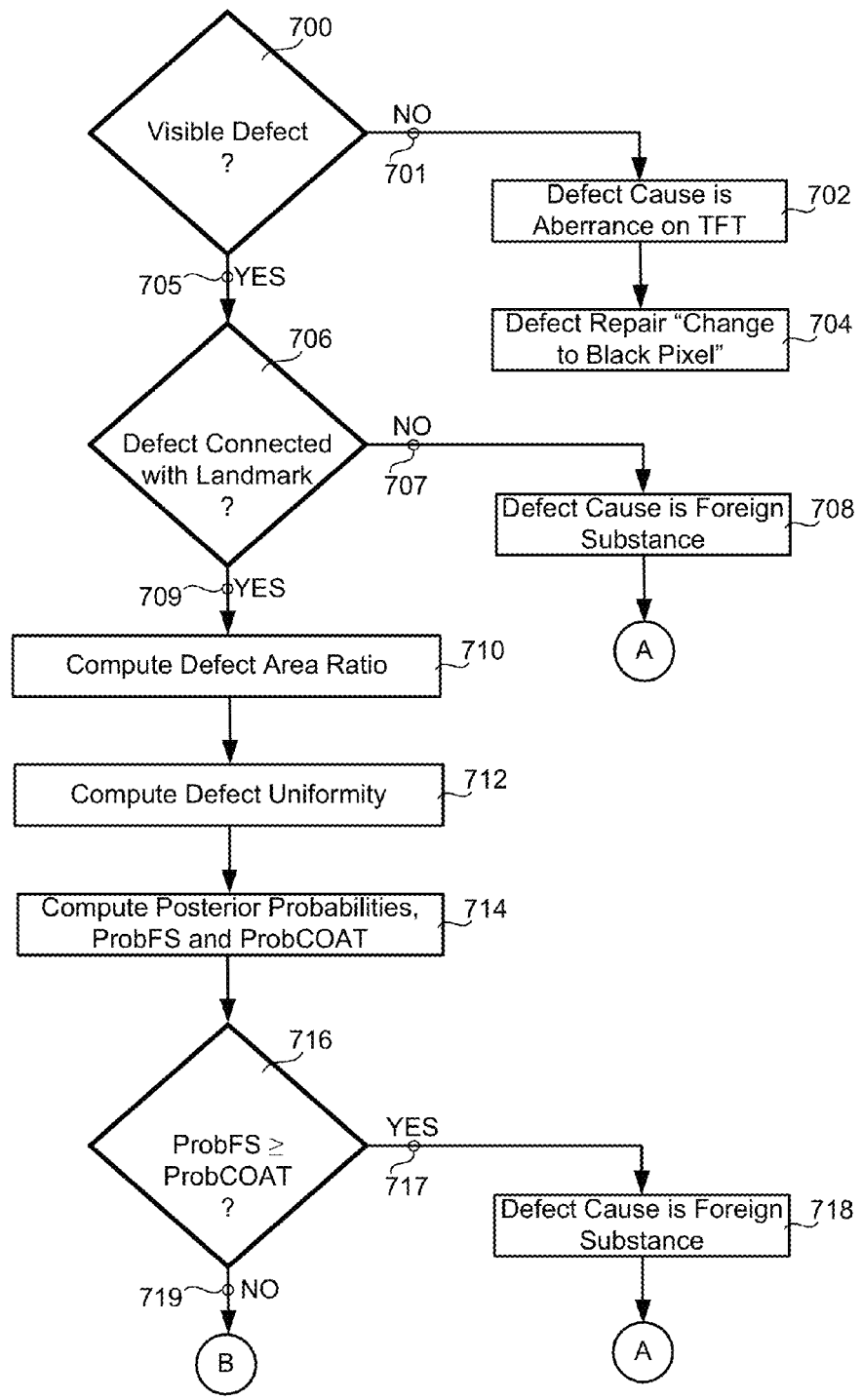
FIG. 7 is a chart showing exemplary embodiments of the present invention comprising defect-cause classification.
Figure 7:
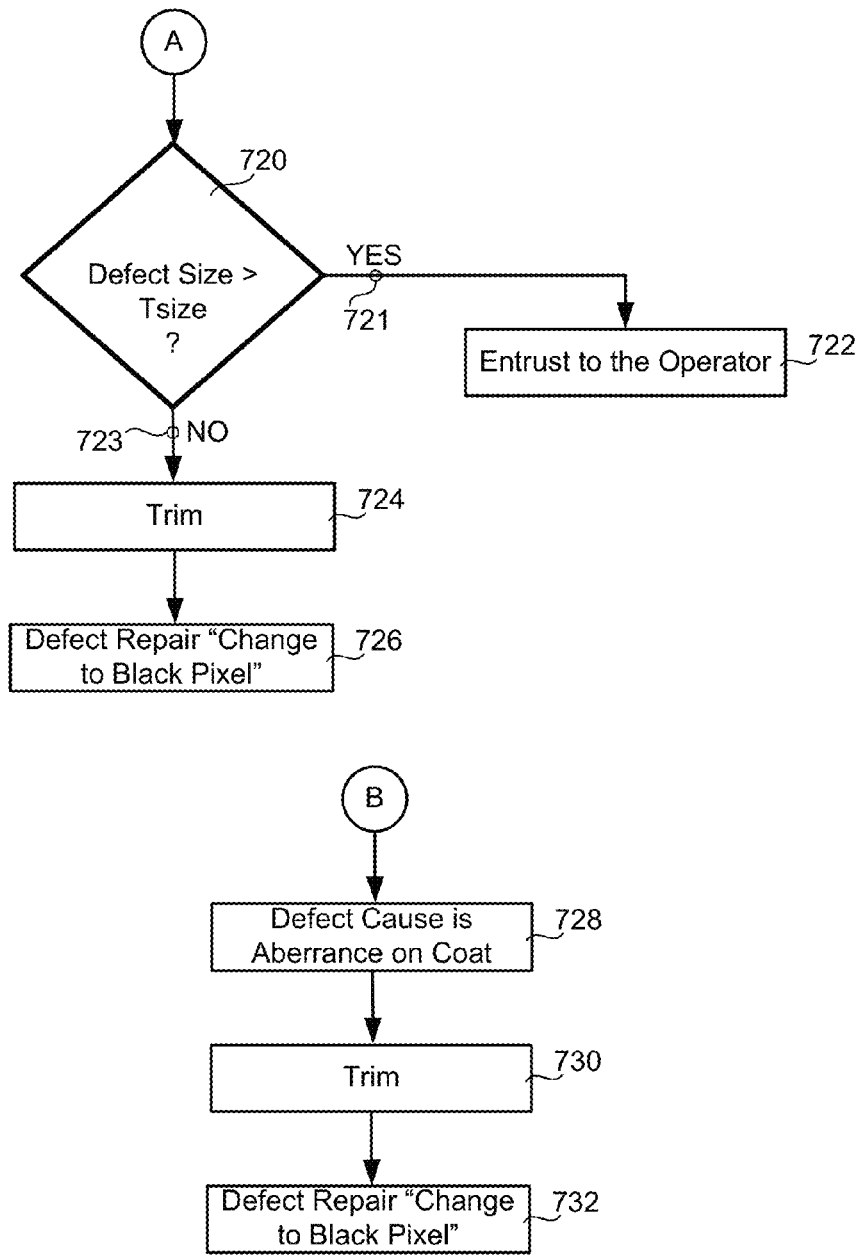

In some embodiments of the present invention, determination of the cause of a defect may combine rule-based, user-defined criteria with learning-based classification. In some embodiments of the present invention, defect cause may be classified as an aberrance on the TFT, as an aberrance on the flat panel coating or as a foreign substance. Some embodiments of defect-type determination may be understood in relation to FIG. 7. In these embodiments, a determination 700 may be made as to whether or not a defect is visible. If the defect is not 701 visible, then the defect cause may be classified 702 as an aberrance on the TFT, and, in some embodiments, the defect repair may be classified 704 as changing the pixel to black. If the defect is 705 visible, then a determination 706 may be made as to whether or not the defect is connected with one of the landmarks. If the defect is not 707 connected with one of the landmarks, then the defect cause may be classified 708 as a foreign substance. If the defect is 709 connected with a landmark, then the defect area ratio may be computed 710 and the defect uniformity may be computed 712. In some embodiments, a normal Bayesian classifier may be used to compute 714 the posterior probability, which may be denoted ProbFS, that the defect cause is a foreign substance and the posterior probability, which may be denoted ProbCOAT, that the defect cause is an aberrance on the flat panel display coat. The posterior probabilities may be compared 716, and if the posterior probability, ProbFS, that the defect cause is a foreign substance is greater than or equal to the posterior probability, ProbCOAT, that the defect cause is an aberrance on the flat panel display coat 717, then the defect cause may be classified 718 as a foreign substance. If the posterior probability, ProbFS, that the defect cause is a foreign substance is not greater than or equal to the posterior probability, ProbCOAT, that the defect cause is an aberrance on the flat panel display coat 719 then the defect cause may be classified 728 as an aberrance on the flat panel display coat, and, in some embodiments, the defect repair may be classified as a trim operation 730 and as changing the pixel to black 732. When the defect cause is classified as a foreign substance 708, 718 the defect size may be compared 720 to a size threshold, which may be denoted Tsize, and when the defect size is greater than the threshold, Tsize, 721, then the defect repair and cause classification may be directed 722 to an operator for manual classification and determination of a repair method. If the defect size is not greater than the threshold, Tsize, 723, then in some embodiments, the defect repair may be classified as a trim operation 724 and as changing the pixel to black 726.

In some embodiments of the present invention comprising a normal Bayesian classifier (NBC), the class conditional probability density function (PDF) of each category may be assumed to be a parametric form. In some embodiments of the present invention, the parametric form of the class conditional PDF may be Gaussian, and, in these embodiments, the PDF of the entire data set (both classes) may therefore be a Mixture of Gaussian with two mixtures. In alternative embodiments, the class conditional PDF of each category may be modeled as a non-parametric density, and, in these embodiments, non-parametric-density estimation methods, for example, kernel density estimation comprising Parzen windowing and other non-parametric-density estimation methods, may be used to estimate the class conditional PDF of each class.

An NBC comprises two stages: off-line training and on-line prediction. In the off-line training process, the parameters, the mean and the covariance, of the class conditional PDF of the features for each category may be estimated from training data. The prior probabilities may be set empirically based on prior knowledge of the occurrence frequency of foreign-substance-caused defects and coat-caused defects. In some embodiments of the present invention, the parameters may be estimated as the sample mean and the sample covariance of the training data. In alternative embodiments of the present invention, the parameters may be estimated using the Expectation-Maximization estimation method for estimation of a maximum-likelihood solution.

Figure 8:
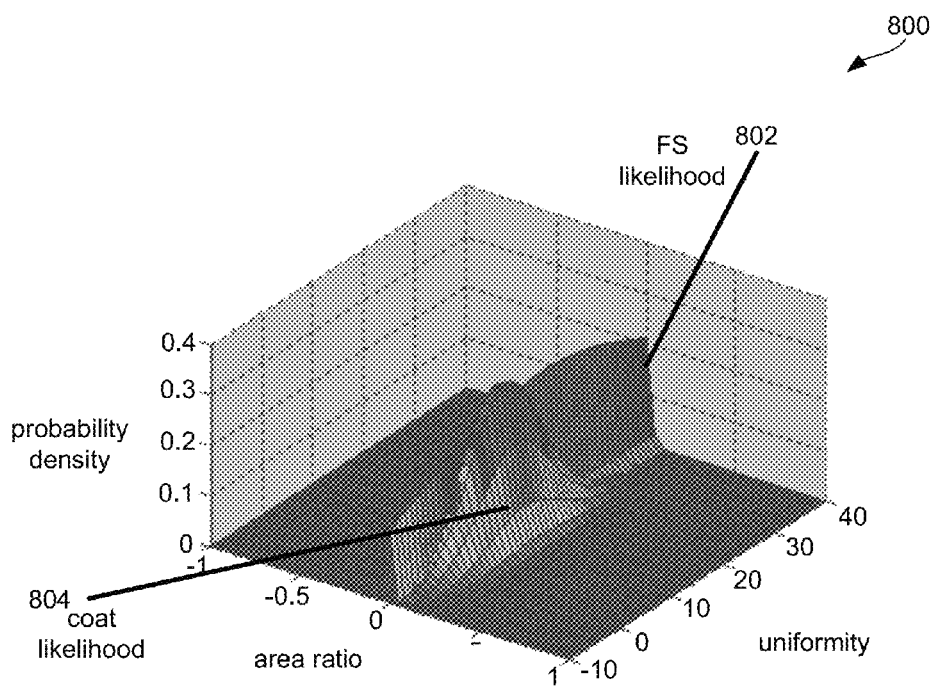
FIG. 8 is a plot of exemplary PDFs for defect-cause classification.
Figure 9:
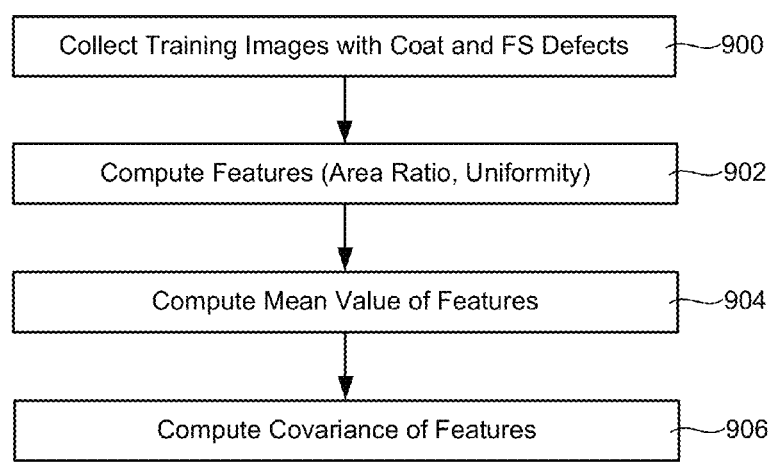
FIG. 9 is a chart showing exemplary embodiments of the present invention comprising PDF estimation.

In the prediction stage, the cause of the defect may be assigned to the class that has the larger posterior probability, thereby basing the classification on the maximum a posteriori probability. Therefore, the Bayesian decision rule may be based on the posterior probabilities:

$$ProbCOAT = p(\text{coat} | x) = \frac{p(x | \text{coat})p(\text{coat})}{p(x | \text{coat})p(\text{coat}) + p(x | FS)p(FS)}$$

and $$ProbFS = p(FS | x) = \frac{p(x | FS)p(FS)}{p(x | \text{coat})p(\text{coat}) + p(x | FS)p(FS)},$$

where x denotes the feature vector comprising the area ratio and the uniformity measure, the likelihoods p(x|coat) and p(x|FS) may be assumed to be Gaussian with parameters $(\mu_{coat}, \sigma_{Coat})$ and $(\mu_{FS}, \sigma_{FS})$, respectively, and p(coat) and p(FS) may denote the prior probabilities. FIG. 8 shows a plot 800 of an exemplary conditional PDF for the defect-cause class foreign substance 802 and an exemplary conditional PDF for the defect-cause class coat 804, both 802, 804 obtained by the training process shown in FIG. 9. Training images with coat-caused defects and foreign-substance-caused defects may be collected 900. Feature values, area ratio and uniformity measure, may be computed 902 for the collected images. The sample mean of the feature values may be computed 904, and the sample covariance of the feature values may be computed 906.

Although the charts and diagrams in the figures may show a specific order of execution, it is understood that the order of execution may differ from that which is depicted. For example, the order of execution of the blocks may be changed relative to the shown order. Also, as a further example, two or more blocks shown in succession in a figure may be executed concurrently, or with partial concurrence. It is understood by those with ordinary skill in the art that software, hardware and/or firmware may be created by one of ordinary skill in the art to carry out the various logical functions described herein.

Some embodiments of the present invention may comprise a computer program product comprising a computer-readable storage medium having instructions stored thereon/in which may be used to program a computing system to perform any of the features and methods described herein. Exemplary computer-readable storage media may include, but are not limited to, flash memory devices, disk storage media, for example, floppy disks, optical disks, magneto-optical disks, Digital Versatile Discs (DVDs), Compact Discs (CDs), micro-drives and other disk storage media, Read-Only Memory (ROMs), Programmable Read-Only Memory (PROMs), Erasable Programmable Read-Only Memory (EPROMS), Electrically Erasable Programmable Read-Only Memory (EEPROMs), Random-Access Memory (RAMS), Video Random-Access Memory (VRAMs), Dynamic Random-Access Memory (DRAMs) and any type of media or device suitable for storing instructions and/or data.

The terms and expressions which have been employed in the foregoing specification are used therein as terms of description and not of limitation, and there is no intention in the use of such terms and expressions of excluding equivalence of the features shown and described or portions thereof, it being recognized that the scope of the invention is defined and limited only by the claims which follow.

What is claimed is:

1. A non-transitory computer-readable medium encoded with a computer program code for implementing a method for identifying a defect type associated with a detected defect in a flat panel display, said method comprising:
  receiving, in a computing device, a defect mask image associated with an image of a detected defect in a flat panel display;
  receiving, in said computing device, a plurality of landmark mask images, wherein:
    each landmark mask image in said plurality of landmark mask images is associated with one of a plurality of landmarks within a flat panel display; and each landmark mask image in said plurality of landmark mask images is extracted from a defect-free model image;

computing a source-defect connectivity measure between said detected defect and a first source line using a first landmark mask image, from said plurality of landmark mask images, associated with said first source line;

computing a gate-defect connectivity measure between said detected defect and a first gate line using a second landmark mask image, from said plurality of landmark mask images, associated with said first gate line;

when said source-defect connectivity measure is not equal to zero or said gate-defect connectivity measure is not equal to zero, identifying a defect type associated with said detected defect based on said source-defect connectivity measure and said gate-defect connectivity measure; and when said source-defect connectivity measure is equal to zero and said gate-defect connectivity measure is equal to zero:
 computing a first distance measure between said detected defect and said first source line;
 computing a second distance measure between said detected defect and a second source line using a third land mark mask image, from said plurality of landmark mask images, associated with said second source line;
 combining said first distance measure and said second distance measure to obtain a source-defect distance measure;
 computing a gate-defect distance measure between said detected defect and said first gate line; and
 identifying said defect type associated with said detected defect based on said source-defect distance measure and said gate-defect distance measure.

2. A computer-readable medium as described in claim 1, wherein, in said method:
 said computing said source-defect connectivity measure comprises determining the number of pixels in said detected defect that overlap said first source line; and
 said computing said gate-defect connectivity measure comprises determining the number of pixels in said detected defect that overlap said first gate line.

3. A computer-readable medium as described in claim 1, wherein, in said method, said defect type is identified as a source-drain leak when said source-defect connectivity measure is greater than said gate-defect connectivity measure.

4. A computer-readable medium as described in claim 1, wherein, in said method, said defect type is identified as a gate-drain leak when said gate-defect connectivity measure is greater than said source-defect connectivity measure.

5. A computer-readable medium as described in claim 1, wherein, in said method, said defect type is identified as a source-drain leak when said gate-defect distance measure is less than source-defect distance measure.

6. A computer-readable medium as described in claim 1, said method further comprising:

computing a TFT-defect connectivity measure between said detected defect and a first TFT using a third landmark mask image, from said plurality of landmark mask images, associated with said first TFT; and setting a flag indicating said detected defect is on said first TFT when said TFT-defect connectivity measure is greater than zero.

7. A computer-readable medium as described in claim 6, said method further comprising:
 receiving a first threshold value; and
 wherein said defect type is identified as a source-drain leak when said gate-defect distance measure is equal to zero and said flag is set and said first source-defect measure is less than said first threshold value.

8. A computer-readable medium as described in claim 6, said method further comprising:
 receiving a first threshold value; and
 wherein said defect type is identified as a gate-drain leak when said gate-defect distance measure is not equal to zero or said flag is not set or said source-defect distance measure is not less than said first threshold value.

9. A computer-readable medium as described in claim 1, wherein said detected defect comprises a first detected defect blob and a second detected defect blob.

10. A computer-readable medium as described in claim 9, wherein:
 the centroid of said first detected defect blob and the centroid of said second detected defect blob are less than a distance threshold apart; and
 a bounding box containing said first detected defect blob and said second detected defect blob overlaps at least one landmark associated with said plurality of landmark mask images.

11. A computer-readable medium as described in claim 1, wherein, in said method:
 said combining said first distance measure and said second distance measure comprises determining the minimum of said first distance measure and said second distance measure; and
 said computing said first distance measure between said detected defect and said first source line comprises:
  finding a bounding box for said detected defect;
  determining an extreme-most point on a first edge of said first source line; and
  computing a distance between an edge of said bounding box and said extreme-most point.

12. A computer-readable medium as described in claim 1, wherein said flat panel display is an LCD display.

13. A computer-readable medium as described in claim 1, said method further comprising identifying a defect cause associated with said detected defect.

14. A computer-readable medium as described in claim 13, said method further comprising associating a repair method with said defect cause associated with said detected defect.

* * * * *